(12) United States Patent
Kim et al.

(10) Patent No.: US 8,008,042 B2
(45) Date of Patent: *Aug. 30, 2011

(54) ASPERGILLUS NIGER PROMOTER FOR EXPRESSING GENES IN HOST CELLS

(75) Inventors: Steve Kim, Palo Alto, CA (US); Edwin Lee, Palo Alto, CA (US); Wei Liu, Palo Alto, CA (US); Huaming Wang, Palo Alto, CA (US)

(73) Assignee: Danisco US Inc., Palo Alto, CA (US)

( * ) Notice: Subject to any disclaimer, the term of this patent is extended or adjusted under 35 U.S.C. 154(b) by 432 days.

This patent is subject to a terminal disclaimer.

(21) Appl. No.: 12/061,539

(22) Filed: Apr. 2, 2008

(65) Prior Publication Data

US 2008/0187964 A1    Aug. 7, 2008

Related U.S. Application Data

(63) Continuation of application No. 10/992,149, filed on Nov. 18, 2004, now Pat. No. 7,378,256.

(51) Int. Cl.
*C12P 21/02* (2006.01)
(52) U.S. Cl. ............... 435/69.1; 435/254.3; 435/320.1; 536/23.4; 536/24.1
(58) Field of Classification Search .................. None
See application file for complete search history.

(56) References Cited

U.S. PATENT DOCUMENTS 5,171,672 A    12/1992    Devchand et al. ........... 435/69.1
7,378,256 B2 *    5/2008    Kim et al. ................... 435/69.1

OTHER PUBLICATIONS

Database EMBL Nov. 4, 2004, Jiang G.; Hu, W.; Lemieux, S. and Roemer, T.; XP002325936 retrieved from EMBL accession No. ADR85583 abstract.
Xinmei, L., "Cloning and characterization of three *Aspergillus niger* promoters," *Gene*, Elsevier Biomedical Press, Amsterdam, NL., V. 163, N. 1, Sep. 22, 1995, pp. 127-131.
Patent Abstracts of Japan, V. 1995, N. 06, Jul. 31, 1995 & JP 07 059571 A (OOZEKI KK), Mar. 7, 1995 abstract.
Yang, Yonghui et al., "Heterologous expression of the single-mutation glucose isomerase (GIG 138P) gene in *Streptomyces lividians* and its genetic instability," *Current Microbiology*, V. 42, Apr. 2001, pp. 241-247.
Database EMBL Nov. 4, 2004, Jiang G.; Hu, W.; Lemieux, S. and Roemer, T., XP002325936 retrieved from EMBL accession No. ADR86170 abstract.

* cited by examiner

*Primary Examiner* — James S Ketter

(57) ABSTRACT

The present invention relates to isolated promoter sequences, particularly a promoter isolated from *Aspergillus niger* designated herein as A4-L or A4 and DNA constructs and vectors including the same.

14 Claims, 8 Drawing Sheets

FIG. 1

A4-L Promoter (SEQ ID NO: 1) -

AAACACCACCCAGCTCGCTGAAAAACAAATCCACAATGCAGGAAATAGGTATCTTA
AATGACGGACATATGCCACTCAAAACGAATGCGTCCTCCCCCTACATCACGATGCAG
CATCCGCAGCCCTTCTCCTTCGGCGGCGGTTCCTGCGCGGTCACCACTGGCGGGCTC
CATTTCGGCTGCAGTGCCGCCTGTGGTGGTTCCTGTACCCGCGGCATCGTGCTGTAG
CCGGTGCCTGAGTTCGGCCGTCCCGACTCCTTGGACGGTGTCTCCAAATTCGGGGTC
TTCTGTGGCTCTTGCACTTCTTTCTTCCTCCTTTTCGTTCTGTTCGATCGGCTCC
GGCTCCACTTCCTTCGGTGCCGGCTTCTCTGTGGGCTTCGGCCCGTCTGGCCCAATG
GCTAGCGGAGCAAACTCCCGATCGAACTTCATGTTCGAGTTCTTGTTCACGTAGAAG
CCGGAGATGTGAGAGGTGATCTGGAACTGCTCACCCTCGTTGGTGGTGACCTGGAGG
TAAAGCAAGTGACCCTTCTGGCGGAGGTGGTAAGGAACGGGGTTCCACGGGGAGAGA
GAGATGGCCTTGACGGTCTTGGGAAGGGGAGCTTCGGCGCGGGGAGGATGGTCTTG
AGAGAGGGGGAGCTAGTAATGTCGTACTTGGACAGGGAGTGCTCCTTCTCCGACGCA
TCAGCCACCTCAGCGGAGATGGCATCGTGCAGAGACAGACCAGCGCTGATACCATGG
AGGTTGTCAACCCGGTCACCCGCAGCGCCAACCAGCTCTCTCATGCGAACAACGTGC
ATACGAGCTTCCTTCTCGTTGTAGGGATCCTGCAGGGCTAACCTGATCCTCTAGGGA
CTTAACAGCAAAGATCACCTGGCGCCGATTGAACCAAGGCGTACAGAACCACTCCAC
AG

A4 Promoter (SEQ ID NO: 2) -

TGCCGGCTTCTCTGTGGGCTTCGGCCCGTCTGGCCCAATGGCTAGCGGAGCAAACTC
CCGATCGAACTTCATGTTCGAGTTCTTGTTCACGTAGAAGCCGGAGATGTGAGAGGT
GATCTGGAACTGCTCACCCTCGTTGGTGGTGACCTGGAGGTAAAGCAAGTGACCCTT
CTGGCGGAGGTGGTAAGGAACGGGGTTCCACGGGGAGAGAGAGATGGCCTTGACGGT
CTTGGGAAGGGGAGCTTCGGCGCGGGGAGGATGGTCTTGAGAGAGGGGGAGCTAGT
AATGTCGTACTTGGACAGGGAGTGCTCCTTCTCCGACGCATCAGCCACCTCAGCGGA
GATGGCATCGTGCAGAGACAGAC

A4-5' Promoter (SEQ ID NO: 3) -

AAACACCACCCAGCTCGCTGAAAAACAAATCCACAATGCAGGAAATAGGTATCTTA
AATGACGGACATATGCCACTCAAAACGAATGCGTCCTCCCCCTACATCACGATGCAG
CATCCGCAGCCCTTCTCCTTCGGCGGCGGTTCCTGCGCGGTCACCACTGGCGGGCTC
CATTTCGGCTGCAGTGCCGCCTGTGGTGGTTCCTGTACCCGCGGCATCGTGCTGTAG
CCGGTGCCTGAGTTCGGCCGTCCCGACTCCTTGGACGGTGTCTCCAAATTCGGGGTC
TTCTGTGGCTCTTGCACTTCTTTCTTCCTCCTTTTCGTTCTGTTCGATCGGCTCC
GGCTCCACTTCCTTCGG

FIG. 2
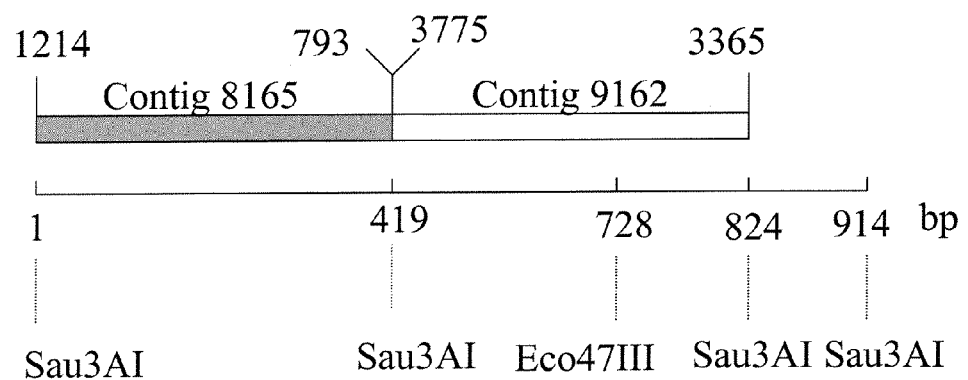
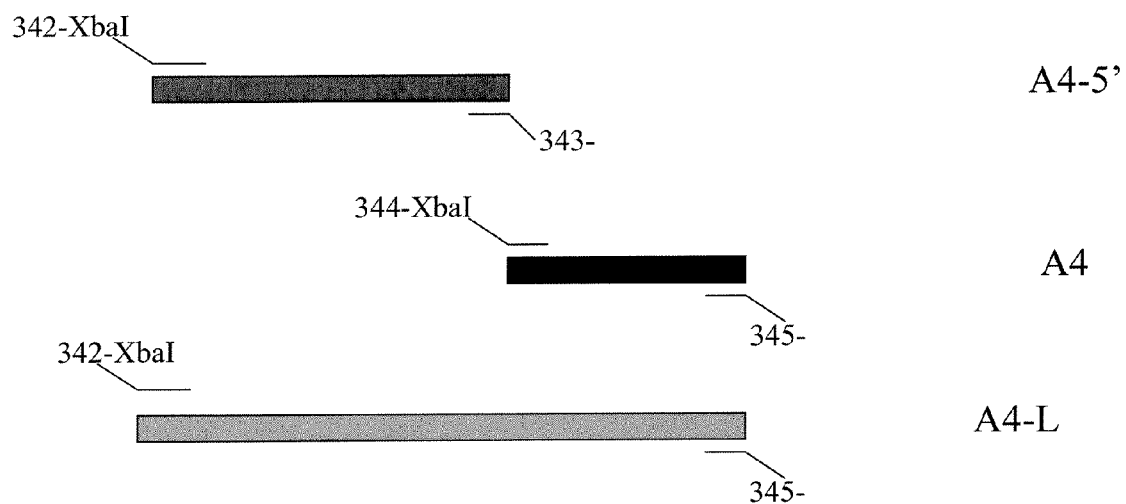

FIG. 4A

DNA sequence of the GI promoter, celA sugnal sequence, 11AG8 mature and 11AG3 terminator.

CTAGAGTCGACCACGCAGGCCGCCAGGTAGTCGACGTTGATCTCGCAGCCGAGCCCGGCC
GGACCGGCGGCGCTGAGCGCGAGGCCGACGGCGGGACGGCCGGCACCGGTACGCGGTGGC
GGGTCGAGTTCGGTGAGCAGCCCACCGGCGATCAGGTCGTCGACGAGCGCGGAGACGGTG
GCCCGGGTGAGCCCGGTGACGGCGGCAACTCCCGCGCGGGAGAGCCGATCTGTGCTGTTT
GCCACGGTATGCAGCACCAGCGCGAGATTATGGGCTCGCACGCTCGACTGTCGGACGGGG
GCACTGGAACGAGAAGTCAGGCGAGCCGTCACGCCCTTGACAATGCCACATCCTGAGCAA
ATAATTCAACCACTAAACAAATCAACCGCGTTTCCCGGAGGTAACCATGGGCTTTGGGAG
CGCTCCCATCGCGTTGTGTCCGCTTCGCACGAGGAGGAACGCTTTGAAACGCCTTTTGGC
CCTGCTCGCGACCGGCGTGTCGATCGTCGGCCTGACTGCGCTAGCCGGCCCCCCGGCACA
GGCCAACCAGCAGATCTGCGACCGCTACGGCACCACCACGATCCAGGACCGGTACGTGGT
GCAGAACAACCGCTGGGGCACCAGCGCCACCCAGTGCATCAATGTGACCGGCAACGGTTT
CGAGATCACCCAGGCCGACGGTTCGGTGCCGACCAACGGCGCCCCGAAGTCCTATCCCTC
GGTCTACGACGGCTGCCACTACGGCAACTGCGCGCCCCGCACGACGCTGCCCATGCGGAT
CAGCTCGATCGGCAGCGCGCCCAGCAGTGTCTCCTACCGCTACACCGGCAACGGCGTCTA
CAACGCCGCGTACGACATCTGGCTGGACCCGACACCCCGCACCAACGGGGTGAACCGGAC
CGAGATCATGATCTGGTTCAACCGGGTCGGCCCGGTCCAGCCCATCGGTTCGCCGGTCGG
CACGGCCCACGTCGGCGGCCGCAGCTGGGAGGTGTGGACCGGCAGCAACGGTTCGAACGA
CGTGATCTCCTTCCTGGCGCCCTCCGCGATCAGCAGCTGGAGCTTCGACGTCAAGGACTT
CGTCGACCAGGCCGTCAGCCACGGCCTGGCCACCCCGGACTGGTACCTCACCAGCATCCA
GGCGGGCTTCGAGCCGTGGGAGGGCGGCACCGGTCTGGCCGTGAACTCGTTCTCCTCCGC
GGTGAACGCCGGGGGCGGGAACGGCGGCACTCCGGGGACACCGGCGGCCTGCCAGGTCTC
CTACAGCACCCACACCTGGCCCGGCGGCTTCACCGTCGACACCACCATCACCAATACCGG
CTCCACACCCGTCGACGGCTGGGAACTGGACTTCACCCTCCCCGCCGGTCACACGGTCAC
CAGCGCGTGGAACGCGCTGATCAGCCCCGCCTCGGGCGCGGTCACGGCACGCAGCACCGG
TTCCAACGGCCGGATCGCGGCCAACGGCGGGACCCAGTCCTTCGGTTTCCAGGGCACCTC
CAGCGGAACGGGGTTCAACGCACCGGCCGGGGCCGGCTCAACGGCACCTCCTGCACAGT
*GAGATGACAATGGGGATCCGCGAGCGGATCGGCTGACCGGAGCGGGGAGGAGGACGGGCG*
*GCCGGCGGAAAAGTCCGCCGGTCCGCTGAATCGCTCCCCGGGCACGGACGTGGCAGTATC*
*AGCGCCATGTCCGGCATATCCCAGCCCTCCGCATG*

FIG. 4B

Protein sequence of the CelA-11AG8 fragment

MGFGSAPIALCPLRTRRNALKRLLALLATGVSIVGLTALAGPPAQANQQICDRYGTTTIQDR
YVVQNNRWGTSATQCINVTGNGFEITQADGSVPTNGAPKSYPSVYDGCHYGNCAPRTTLPMR
ISSIGSAPSSVSYRYTGNGVYNAAYDIWLDPTPRTNGVNRTEIMIWFNRVGPVQPIGSPVGT
AHVGGRSWEVWTGSNGSNDVISFLAPSAISSWSFDVKDFVDQAVSHGLATPDWYLTSIQAGF
EPWEGGTGLAVNSFSSAVNAGGGNGGTPGTPAACQVSYSTHTWPGGFTVDTTITNTGSTPVD
GWELDFTLPAGHTVTSAWNALISPASGAVTARSTGSNGRIAANGGTQSFGFQGTSSGTFNA
PAGGRLNGTSCTVR

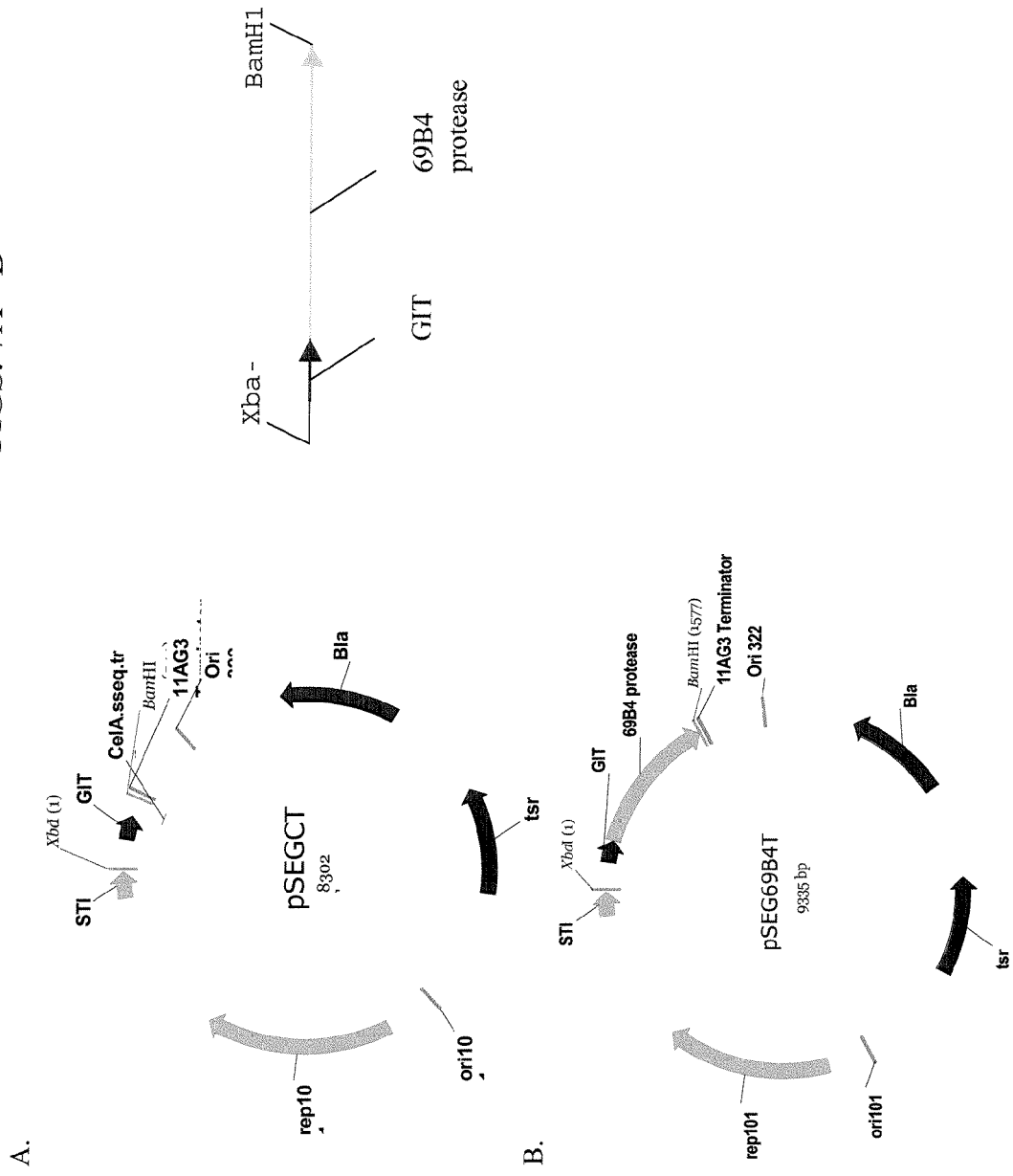
FIGS. 7A - B

ASPERGILLUS NIGER PROMOTER FOR EXPRESSING GENES IN HOST CELLS

This application is a continuation of U.S. patent application Ser. No. 10/992,149, filed Nov. 18, 2004, now U.S. Pat. No. 7,378,256 the contents of which are incorporated by reference in their entirety.

BACKGROUND OF THE INVENTION

1. Field of the Invention

The present invention relates to isolated promoters and to nucleic acid constructs and vectors comprising the promoters. The invention also relates to methods for expressing a coding sequence of interest in a host cell.

2. Description of the Related Art

Molecular biotechnology is a discipline that is based on the ability of researchers to transfer specific units of genetic information from one organism to another with the goal of producing commercially relevant amounts of useful products. One of the goals of this cloning process is to achieve maximum expression of the cloned gene. Recombinant production of a product encoded by a gene is accomplished by constructing expression vectors suitable for use in a host cell in which the nucleic acid coding for a desired product is placed under the expression control of a promoter. The expression vector is introduced into a host cell by various techniques, such as transformation, and production of the desired product is then achieved by culturing the transformed host cell under suitable conditions necessary for the functioning of the promoter included in the expression vector.

While numerous promoters are known in the art, there is a need for new promoters, which control the expression of heterologous genes and coding sequences. This invention describes new promoters used to express genes in host cells, such as bacterial and fungal cells.

SUMMARY OF THE INVENTION

The present invention relates to isolated promoter sequences, constructs, vectors and host cells comprising one or more of the promoter sequences operably linked to a heterologous coding sequence.

The present invention also relates to isolated promoter sequences selected from the group consisting of
- a) SEQ ID NO: 1;
- b) a subsequence of SEQ ID NO: 1 that retains promoter activity;
- c) a subsequence of SEQ ID NO: 2 that retains promoter activity;
- d) a nucleic acid sequence that functions as a promoter and hybridizes under medium, high or very high stringency conditions with SEQ ID NO: 1; SEQ ID NO: 2 or a subsequence thereof;
- e) a hybrid promoter sequence comprising SEQ ID NO: 2 or a subsequence thereof;
- f) a tandem promoter sequence comprising SEQ ID NO: 2; and
- g) a variant promoter sequence comprising deletions, substitutions or insertions of a parent promoter, wherein the parent promoter is SEQ ID NO: 1 or SEQ ID NO: 2.

BRIEF DESCRIPTION OF THE FIGURES

FIG. 1 shows the DNA sequence of the *Aspergillus niger* A4 long promoter (A4-L promoter) (SEQ ID NO: 1), the DNA sequence of the *Aspergillus niger* A4 promoter (SEQ ID NO: 2) and the DNA sequence of the *Aspergillus niger* A4-5' promoter (SEQ ID NO:3).

FIG. 2 is a diagram of the A4-L promoter, which comprises two contiguous regions, contig 8165 and contig 9162 obtained from an ERGO database search and a BLAST database search. These contiguous regions are located in different regions of the *Aspergillus* chromosome. Contig 8165 is 3988 bp and contig 9162 is 8140 bp. The first 419 bp of the A4-L promoter is found from 1214 bp to 793 bp of contig 8165 (herein designated the A4-5' promoter, (SEQ ID NO: 3)). The second part of the A4-L promoter (bp 420 to 829) (herein designated the A4 promoter (SEQ ID NO: 2)) is located at 3775 to 3365 bp of contig 9162. Restriction sites which were used to make the two truncated fragments (A4 (SEQ ID NO: 2) and A4-5' (SEQ ID NO: 3) are shown.

FIGS. 4A-B provide the DNA sequence (SEQ ID NO: 4) of the expression cassette consisting of the glucose isomerase (GIT) promoter, celA signal sequence, 11AG8 mature cellulase sequence and 11AG3 terminator (FIG. 4A), and the protein sequence (SEQ ID NO: 5) of the CelA-11AG8 (FIG. 4B). The celA signal sequence is underlined and the 11AG3 terminator sequence is in italics in FIG. 4A.

FIGS. 7A-B show the pSEG69B4 vector with a GI promoter and the pSEA469B4T vector with the A4 promoter (SEQ ID NO: 2) of the invention.

DETAILED DESCRIPTION OF THE INVENTION

Definitions

Figure 3:
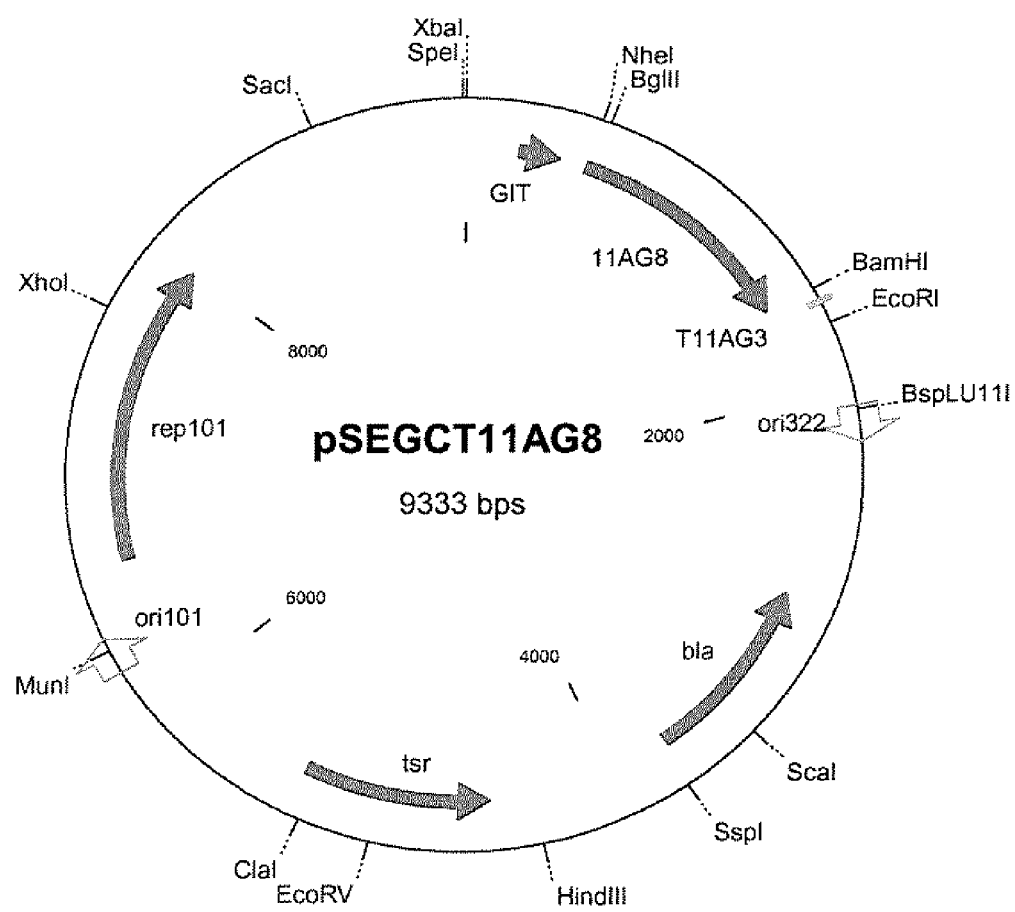
FIG. 3 shows the pSEGCT11AG8 vector which includes: a glucose isomerase promoter derived from *Actinoplanes missouriensis*, a signal sequence of *S. lividans* cellulase, celA, a polynucleotide encoding a cellulase 11AG8 gene from an *Actinomyces* species, a cellulase 11AG3 terminator sequence.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with general dictionaries of many of the terms used in this invention. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

The term "promoter" is defined herein as a DNA sequence that binds RNA polymerase and directs the polymerase to the correct downstream transcription start site of a coding sequence of interest resulting in transcription. The term "promoter" is also understood to include the 5'non-coding region (between the promoter and translation start) for translation after transcription into mRNA and cis-acting transcription control elements, such as enhancers. In preferred embodiments, the promoter will be effective in *Streptomyces* to express a coding region of interest.

The term "variant promoter" is defined herein as a promoter having a nucleic acid sequence comprising a substitution, deletion and/or insertion in one or more nucleotides of a parent promoter, wherein the variant promoter has more or less promoter activity than the corresponding parent promoter. The term "variant promoter" includes natural variants and in vitro generated variants.

The term "hybrid promoter" as defined herein means parts of two or more promoters which are fused together resulting in a sequence which is a fusion of two or more promoters and having promoter activity which results in the transcription of a coding sequence of interest.

The term "tandem promoter" is defined herein as two or more promoters each of which is operably linked to a coding sequence of interest.

The term "isolated" as defined herein means a compound, a protein, cell, nucleic acid sequence or amino acid that is removed from at least one component with which it is naturally associated.

The term "coding sequence of interest" is defined herein as a nucleic acid sequence that is transcribed into mRNA which is translated into a polypeptide when placed under the control of appropriate control sequences including a promoter. A coding sequence of interest may include cDNA, genomic DNA, synthetic DNA and recombinant DNA. A coding sequence of interest is generally determined by the ATG start codon located just upstream of the open reading frame at the 3' end of the RNA.

The term "heterologous" in general means that a polynucleotide or polypeptide does not naturally occur in a host cell. The term "heterologous" with reference to a coding sequence, such as a "heterologous coding sequence" means that a promoter encompassed by the invention is not naturally operably linked with the coding sequence in a native host cell.

The term "operably linked" refers to juxtaposition, wherein elements are in an arrangement allowing them to be functionally related. For example, a promoter is operably linked to a coding sequence of interest if it controls the transcription of the sequence.

The term "nucleic acid sequence" encompasses DNA, RNA, single or doubled stranded and modification thereof. The terms "nucleic acid sequence" and "polynucleotide" may be used interchangeability herein.

The term "DNA construct" as used herein means a nucleic acid sequence, which comprises at least two DNA polynucleotide fragments.

As used herein, the term "reporter gene" refers to a nucleotide sequence, which is capable of expression in cells and where expression of the reporter confers to cells containing the expressed gene, the ability to be easily detected and measured.

The term "signal sequence" or "signal peptide" refers to a sequence of amino acids at the N-terminal portion of a protein, which facilitates the secretion of the mature form of the protein outside the cell. The mature form of the extracellular protein lacks the signal sequence which is cleaved off during the secretion process.

The term "vector" is defined herein as a polynucleotide designed to carry nucleic acid sequences to be introduced into one or more cell types. Vectors include cloning vectors, expression vectors, shuttle vectors, plasmids, phage or virus particles, DNA constructs, cassettes and the like. Typical expression vectors, which also include plasmids include regulatory sequences such as promoters, signal sequences, a gene of interest and transcription terminators.

As used herein, "polypeptide," "peptide" and "protein" are used interchangeably and include reference to a polymer of amino acid residues. The terms apply to amino acid polymers in which one or more amino acid residue is an artificial chemical analog of a corresponding naturally occurring amino acid, as well as to naturally occurring amino acid polymers. The terms also apply to polymers containing conservative amino acid substitutions such that the polypeptide remains functional.

"Host cell" means a cell which has the capacity to act as a host and expression vehicle for a vector according to the invention. In some embodiments of the invention, "host cell" means bacterial and fungal cells.

"Transformation" means introducing DNA into an organism so that the DNA is maintained either as an extrachromosomal element or chromosomal integrant.

Preferred Embodiments

A. Promoters

In a preferred embodiment, a promoter has the nucleic acid sequence of nucleotides 1-914 of SEQ ID NO: 1 or a subsequence thereof. The subsequence will retain promoter activity and preferably contain at least about 100 nucleotides, at least about 200 nucleotides; at least about 250 nucleotides; at least about 300 nucleotides; at least about 400 nucleotides; at least about 350 nucleotides; at least about 450 nucleotides; at least about 500 nucleotides; at least about 550 nucleotides and at least about 600 nucleotides.

In another preferred embodiment, the promoter has the nucleic acid sequence of nucleotides 1-365 of SEQ ID NO: 2 or a subsequence thereof. The subsequence will retain promoter activity and preferably contains at least about 100 nucleotides, at least about 150 nucleotides; at least about 200 nucleotides; at least about 250 nucleotides; at least about 300 nucleotides, at least about 350 nucleotides, and at least about 360 nucleotides.

The promoter may also be a hybrid promoter comprising a portion of one or more promoters of the present invention; a portion of a promoter of the present invention and a portion of another promoter. In some preferred embodiments, the hybrid promoter will include a subsequence of SEQ ID NO: 2 having at least about 100 nucleotides, at least about 150 nucleotides;

at least about 200 nucleotide; at least about 250 nucleotides; at least about 300 nucleotides and at least about 350 nucleotides of SEQ ID NO: 2.

The other promoter of the hybrid promoter may be any promoter that shows promoter activity in a host cell, and includes mutant promoters, truncated promoters and the like which may or may not be native to the host cell. Examples of other promoters, which may be useful in a hybrid promoter of the invention, include fungal and bacterial promoters. Some specific nonlimiting examples include; the aprE promoter or a mutant aprE promoter (WO 01/51643); the aph promoter of the *Streptomyces fradiae* aminoglycoside 3'-phosphotransferase gene; an *Aspergillus niger* glucoamylase (glaA) promoter; the glucose isomerase (GI) promoter of *Actinoplanes missouriensis* and the derivative GI (GIT) promoter (U.S. Pat. No. 6,562,612 and EPA 351029); the glucose isomerase (GI) promoter from *Streptomyces lividans* (SEQ ID NO: 1 in WO 03/089621), the short wild-type GI promoter (SEQ ID NO: 33 in WO 03/089621), the 1.5 GI promoter (SEQ ID NO: 31 in WO 03/089621), the 1.20 GI promoter (SEQ ID NO: 32), or any of the variant GI promoters (SEQ ID NOs: 9-28 in WO 03/089621) as disclosed in WO 03/089621; the cbh1, cbh2, egl1 and egl2 promoters from filamentous fungi and specifically the *Trichoderma reesei* cellobiohydrolase promoter (GenBank Accession No. D86235); the lacZ and tac promoters (Bagdasarion et al., 1983, *Gene* 26:273-282); the ermE promoter (Ward et al., 1986, *Mol. Gen. Genet.* 203:468-478 and Schmitt-John et al., 1992, *Appl. Microbiol. Biotechnol.* 36:493-498); and the *Bacillus subtilis* phage ø29 promoters (Pulido et al., 1986, *Gene* 49:377-382). Promoters effective in *Streptomyces* are listed in Hopwood et al., (Hopwood et al., Regulation of Gene Expression in Antibiotic-producing *Streptomyces*. In Booth, I. and Higgins, C. (Eds) SYMPOSIUM OF THE SOCIETY FOR GENERAL MICROBIOLOGY, REGULATION OF GENE EXPRESSION, Cambridge University Press, 1986 pgs. 251-276). *Streptomyces* phage promoters are also disclosed in Labes et al., 1997, *Microbiol.* 143:1503-1512. Other promoters which may be effective for use in the hybrid promoters herein are promoters listed in Deuschle et al., 1986 *EMBO J.* 5:2987-2994 and WO 96/00787.

In some preferred embodiments, the hybrid promoter will include a subsequence of SEQ ID NO: 2 and a portion of a GI promoter or variant GI promoter. In other embodiments, the hybrid promoter will include a subsequence of SEQ ID NO: 2 and a native promoter obtained from the genes of a *Streptomyces* spp. and particularly a *S. lividans* strain.

The promoter may also be a tandem promoter, which comprises two or more promoters. In some embodiments, the tandem promoter will include the promoter of SEQ ID NO: 2 or a subsequence thereof and one or more other promoters such as those discussed above for hybrid promoters.

While the other promoter, comprising a hybrid promoter or a tandem promoter, may be native to a coding sequence of interest in a host cell, the promoters encompassed by the invention are not native to the coding sequence in a host cell.

In some embodiments, the promoter is a variant promoter of a parent promoter having the sequence of SEQ ID NO: 1, SEQ ID NO: 2 or a subsequence thereof. A variant promoter will include one or more (e.g. 1, 2, 3 or 4) changes in the nucleotide sequence of SEQ ID NO: 1, SEQ ID NO: 2 or a subsequence thereof, which is a deletion, substitution or insertion, wherein the variant has promoter activity. In a preferred embodiment, the variant promoter will include one change from the parent promoter. Methods for obtaining variant promoters are well-known in the art and include hybridizing a nucleic acid sequence under various stringency conditions with SEQ ID NO: 1 or SEQ ID NO: 2, site-directed mutagenesis; digestion with PCR amplification; and DNA shuffling (Carter et al., 1985 *NAR* 13:4431-4443; Wells et al., 1986, *Phil. Trans. R. Soc. Lond.* 317:415-423 and Zoller et al., 1982 *NAR* 10:6487-6500).

A hybrid promoter, a tandem promoter, a variant promoter, a promoter which is a subsequence of SEQ ID NO: 1 or SEQ ID NO: 2 or a nucleic acid sequence which hybridizes with SEQ ID NO: 1 or SE ID NO: 2 will have at least about 20%, at least about 30%, at least about 40%, least about 50%, at least about 60%, at least about 80%, and at least about 100% of the promoter activity of the promoter of SEQ ID NO: 1 or SEQ ID NO: 2. In some embodiments, the promoter activity will be greater, for example more than about 100%, more than about 150%, more than about 200% and more than about 250%.

In some embodiments, the promoter will include a nucleic acid sequence that hybridizes under medium, high or very high stringency conditions with SEQ ID NO: 1; SEQ ID NO: 2 or a subsequence thereof.

In a preferred embodiment, hybridization is used to analyze whether a given DNA fragment corresponds to a promoter DNA sequence described herein and thus falls within the scope of the present invention. Sambrook et al., MOLECULAR CLONING: A LABORATORY MANUAL ($2^{nd}$ Ed., 1989 Cold Spring Harbor, N.Y.) describes general hybridization methods.

"Hybridization conditions" refer to the degree of "stringency" of the conditions under which hybridization is measured. Hybridization conditions can be based on the melting temperature (Tm) of the nucleic acid binding complex, as taught in Berger and Kimmel (1987, Guide to Molecular Cloning Techniques, METHODS IN ENZYMOLOGY, Vol 152, Academic Press, San Diego Calif.). Hybridization conditions can also be based on the washing conditions employed after hybridization as known in the art.

"Low-stringency" conditions refer to washing with a solution of 0.2×SSC/0.1% SDS at 20° C. for 15 minutes. "Medium-stringency" conditions refer to washing with a solution of 0.2×SSC/0.1% SDS at 37° C. for 30 minutes. "High-stringency" conditions refer to washing with a solution of 0.2×SSC/0.1% SDS at 37° C. for 45 minutes. "Very high-stringency" conditions refer to washing with a solution of 0.2×SSC/0.1% SDS at 37° C. for 60 minutes.

Another aspect of the invention is use of hybridization conditions based on the melting temperature (Tm) of the nucleic acid binding complex, as taught in Berger and Kimmel (1987, Guide to Molecular Cloning Techniques, METHODS IN ENZYMOLOGY, Vol. 152, Academic Press, San Diego, Calif. "Very high stringency" typically occurs at about Tm-5° C. (5° C. below the Tm of the probe); "high stringency" typically occurs at about 5° C. to 10° C. below Tm; "medium stringency" at about 10° C. to 20° C. below Tm; and "low stringency" at about 20° C. to 25° C. below Tm.

A hybridization assay is essentially as follows: Genomic DNA from a particular target source is fragmented by digestion with an appropriate restriction enzyme, e.g., EcoR I, Hind III, Bam HI, Cla I, Kpn I, Mlu I, Spe I, Bgl II, Nco I, Xba I, Xho I and Xma I (supplied by New England Biolabs, Inc., Beverly, Mass. and Boehringer Mannheim) according to the manufacturer's instructions. The samples are then electrophoresed through an agarose gel (for example, 0.8% agarose) so that separation of DNA fragments can be visualized by size. DNA fragments are typically visualized by ethidium bromide staining. The gel may be briefly rinsed in distilled $H_2O$ and subsequently depurinated in an appropriate solution (such as, for example, 0.25M HCl) with gentle shaking followed by denaturation for 30 minutes (in, for example, 0.4 M NaOH) with gentle shaking. A renaturation step may be included, in which the gel is placed in 1.5 M NaCl, 1MTris, pH 7.0 with gentle shaking for 30 minutes. The DNA should then be transferred onto an appropriate positively charged membrane, for example, *Maximum Strength Nytran Plus* membrane (Schleicher & Schuell, Keene, N.H.), using a transfer solution (such as, for example, 6×SSC (900 mM NaCl, 90 mM trisodium citrate). Once the transfer is complete, generally after about 2 hours, the membrane is rinsed in e.g., 2×SSC (2×SSC=300 mM NaCl, 30 mM trisodium citrate) and air dried at room temperature. The membrane should then be prehybridized (for approximately 2 hours or more) in a suitable prehybridization solution (such as, for example, an aqueous solution containing per 100 mL: 20-50 mL formamide, 25 mL of 20×SSPE (1×SSPE=0.18 M NaCl, 1 mM EDTA, 10 mM $NaH_2PO_4$, pH 7.7), 2.5 mL of 20% SDS, and 1 mL of 10 mg/mL sheared herring sperm DNA). As would be known to one of skill in the art, the amount of formamide in the prehybridization solution may be varied depending on the nature of the reaction obtained according to routine methods. Thus, a lower amount of formamide may result in more complete hybridization in terms of identifying hybridizing molecules than the same procedure using a larger amount of formamide. On the other hand, a strong hybridization band may be more easily visually identified by using more formamide.

A DNA probe generally between 50 and 500 bases in length taken from the sequences in FIG. 1 should be isolated by electrophoresis in an agarose gel, the fragment excised from the gel, and recovered from the excised agarose. For a more detailed procedure, see Sambrook, supra. This purified fragment of DNA is then labeled (using, for example, the Megaprime labeling system according to the instructions of the manufacturer) to incorporate $P^{32}$ in the DNA. The labeled probe is denatured by heating to 95° C. for 5 minutes and immediately added to the membrane and prehybridization solution. The hybridization reaction should proceed for an appropriate time and under appropriate conditions, for example, for 18 hours at 37° C. with gentle shaking or rotating. The membrane is rinsed (for example, in 2×SSC/0.3% SDS) and then washed in an appropriate wash solution with gentle agitation. The stringency desired will be a reflection of the conditions under which the membrane (filter) is washed.

In one preferred embodiment, the nucleic acid sequence will be the sequence of SEQ ID NO: 2 and the hybridization stringency conditions will be high.

In other embodiments, a promoter according to the invention will be a subsequence having at least 80%, at least 85%, at least 90%, at least 95%, at least 96%, at least 97%, at least 98% and at least 99% sequence identity with SEQ ID NO: 1 or SEQ ID NO: 2.

The term "identity" in the context of two nucleic acid sequences or polypeptides refers to nucleotides or amino acid residues in the two sequences that are the same when aligned for maximum correspondence, as measured using one of the following "sequence comparison algorithms." Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

An example of an algorithm that is suitable for determining sequence similarity is the BLAST algorithm, which is described in Altschul, et al., *J. Mol. Biol.* 215:403-410 (1990). Software for performing BLAST analyses is publicly available through the National Center for Biotechnology Information available on the world wide web (www) ncbi.nlm.nih.gov. The BLAST algorithm performs a statistical analysis of the similarity between two sequences (see, e.g., Karlin & Altschul, *Proc. Nat'l. Acad. Sci. USA* 90:5873-5787 (1993)).

B. Coding Sequences of Interest

The promoters encompassed by the invention are operably linked to a coding sequence of interest. The polypeptide encoded by the coding sequence may be an enzyme, a hormone, a growth factor, an antibiotic or portion thereof, a receptor or portion thereof, a reporter gene or other secondary metabolites.

In some embodiments, the enzyme is a cellulase, a hemicellulase, a xylanase, a amylase, a glucoamylase, a cutinase, a phytase, a laccase, a lipase, a protease, an isomerase, an esterase and the like originating from bacteria or fungi.

In some particularly preferred embodiments, the enzyme is a cellulase. Cellulases are enzymes that hydrolyze the β-D-glucosidic linkages in celluloses. Cellulolytic enzymes have been traditionally divided into three major classes: endoglucanases, exoglucanases or cellobiohydrolases and β-glucosidases (Knowles, J. et al., *TIBTECH* 5:255-261 (1987)). Numerous cellulases have been described in the scientific literature, examples of which include: from *Trichoderma reesei*: Shoemaker, S. et al., *Bio/Technology*, 1:691-696, 1983, which discloses CBHI; Teeri, T. et al., *Gene*, 51:43-52, 1987, which discloses CBHII; Penttila, M. et al., *Gene*, 45:253-263, 1986, which discloses EGI; Saloheimo, M. et al., *Gene*, 63:11-22, 1988, which discloses EGII; Okada, M. et al., *Appl. Environ. Microbiol.*, 64:555-563, 1988, which discloses EGIII; Saloheimo, M. et al., *Eur. J. Biochem.*, 249:584-591, 1997, which discloses EGIV; and Saloheimo, A. et al., *Molecular Microbiology*, 13:219-228, 1994, which discloses EGV. Exo-cellobiohydrolases and endoglucanases from species other than *Trichoderma* have also been described e.g., Ooi et al., 1990, which discloses the cDNA sequence coding for endoglucanase F1-CMC produced by *Aspergillus aculeatus*; Kawaguchi T et al., 1996, which discloses the cloning and sequencing of the cDNA encoding beta-glucosidase 1 from *Aspergillus aculeatus*; Sakamoto et al., 1995, which discloses the cDNA sequence encoding the endoglucanase CMCase-1 from *Aspergillus kawachii* IFO 4308; and Saarilahti et al., 1990 which discloses an endoglucanase from *Erwinia carotovara*.

In a particularly preferred embodiment, the cellulase to be expressed by a promoter of the invention is a cellulase disclosed in U.S. Pat. No. 6,287,839 and U.S. Pat. No. 6,562,612. Particularly preferred cellulases are cellulases comprising an amino acid sequence of SEQ ID NO: 1, a fragment or a derivative thereof having cellulolytic activity and greater than 70% sequence identity to an active portion of SEQ ID NO: 1 of U.S. Pat. No. 6,562,612.

In other particularly preferred embodiments, the enzyme is a protease, such as a serine, metallo, thiol or acid protease. In some embodiments, the protease will be a serine protease (e.g., subtilisin). Serine proteases are well known in the art and reference is made to Markland, et al. (1983) Honne-Seyler's Z Physiol. Chem 364:1537-1540; Drenth, J. et al. (1972) *Eur. J. Biochem.* 26:177-181; U.S. Pat. Nos. 4,760,025 (RE 34,606), 5,182,204 and 6,312,936 and EP 0 323,299). Means for measuring proteolytic activity are disclosed in K. M. Kalisz, "Microbial Proteinases" ADVANCES IN BIOCHEMICAL ENGINEERING AND BIOTECHNOLOGY, A. Fiecht Ed. 1988.

In some embodiments, the hormone is a follicle-stimulating hormone, luteinizing hormone, corticotropin-releasing factor, somatostatin, gonadotropin hormone, vasopressin, oxytocin, erythropoietin, insulin and the like.

In some embodiments, the growth factor, which is a protein that binds to receptors on the cell surface with the primary result of activating cellular proliferation and/or differentiation, include platelet-derived growth factor, epidermal growth factor, nerve growth factor, fibroblast growth factor, insulin-like growth factors, transforming growth factors and the like.

In some embodiments, the growth factor is a cytokine. Cytokines include but are not limited to colony stimulating factors, the interleukins (IL-1 ($\alpha$ and $\beta$), IL-2 through IL-13) and the interferons ($\alpha$, $\beta$ and $\gamma$).

In some embodiments, the antibodies include, but are not limited to, immunoglobulins from any species from which it is desirable to produce large quantities, It is especially preferred that the antibodies are human antibodies. Immunoglobulins may be from any class, i.e. G, A, M, E or D.

The coding sequence may be either native or heterologous to a host cell. In addition, the coding sequence may encode a full-length protein, such as a cellulase or a truncated form of a full-length protein. The invention is not limited to a particular coding sequence but encompasses numerous coding sequences, which are operably linked to a promoter of the invention.

C. Signal Sequences

In some embodiments, especially when the coding sequence of interest codes for an extracellular enzyme, such as a cellulase, protease or starch degrading enzyme, a signal sequence may be linked to the N-terminal portion of the coding sequence. The signal may be used to facilitate the secretion of a DNA sequence. The signal sequence may be endogenous or exogenous to the host organism. The signal sequence may be one normally associated with the encoded polypeptide. In some embodiments, the signal sequence comprises a signal sequence from a *Streptomyces* cellulase gene. In one embodiment, a preferred signal sequence is a *S. lividans* cellulase, celA (Bently et al., (2002) *Nature* 417:141-147). However, one skilled in the art is aware of numerous signal peptides which may be used depending on a protein to be expressed and secreted in a host organism.

D. DNA Constructs and Vectors

The nucleic acid construct of the invention comprising a coding region of interest may be prepared synthetically by established standard methods, e.g., the phosphoramidite method described by Beaucage and Caruthers, (1981) *Tetrahedron Letters* 22:1859-1869, or the method described by Matthes et al., (1984) *EMBO Journal* 3: 801-805. The nucleic acid construct may be of mixed synthetic and genomic origin and may be prepared by ligating fragments of synthetic or genomic DNA. The nucleic acid construct may also be prepared by polymerase chain reaction using specific primers, for instance as described in U.S. Pat. No. 4,683,202 or Saiki et al., *Science* 239 (1988), 487-491.

A DNA construct of the invention may be inserted into a vector, such as an expression vector. A variety of vectors suitable for the cloning, transformation and expression of polypeptides in fungus, yeast and bacteria are known by those of skill in the art. Typically, the vector or cassette will contain a promoter of the invention, optionally a signal sequence, a coding region of interest and a terminator sequence. In preferred embodiments, the vector will include one or more cloning sties located between the signal sequence and the terminator sequences.

In some preferred embodiments, when a cellulase gene is transferred into a *Streptomyces* host cell, transformation includes use of a vector including a promoter of the invention, a nucleic acid coding for a signal sequence derived from a *Streptomyces* cellulase gene, preferably a *Streptomyces lividans* cellulase gene, and a polynucleotide encoding a bacterial cellulase, particularly a cellulase gene derived from a *Streptomyces* strain, most particularly a *S. lividans* cellulase gene. The signal sequence may also be derived from other signal sequences of a *Streptomyces* strain, and in patricianly *S. lividans*.

Exemplary vectors that may be used in the practice of the invention include pSEGCT pSEGCT11AG8, and pSEACT. Construction of such vectors is well known in the art and reference is made to U. S. Pat. No. 6,287,839; U.S. Pat. No. 6,562,612 and International Publication No. WO 02/50245. Construction of pSEGCT involves the use of two plasmids pIJ486, which is described in Ward et al., (1986) *Mol. Gen. Genet.* 203:468-478 and pIJ488, which is described in Yanisch-Perron et al., (1985) *Gene* 33: 103-119. In addition, reference is made to Hopwood et al., (1983) *J. Gen. Microbiol.* 129:2257-2260. Other vectors that may be used include pSEG69B4 and pSEA469B4T as described in the examples.

E. Transformation

A vector of the invention will be transformed into a host cell. General transformation techniques are known in the art (Ausubel et al., 1994, CURRENT PROTOCOLS IN MOLECULAR BIOLOGY and Campbell et al., 1989 *Curr. Genet* 16:53-56). Some of these general techniques include, but are not limited to the use of a particle or gene gun (biolistics), permeabilization of filamentous fungi cells walls prior to the transformation process (e.g., by use of high concentrations of alkali, e.g., 0.05 M to 0.4 M $CaCl_2$ or lithium acetate), protoplast fusion, electroporation, or agrobacterium mediated transformation (U.S. Pat. No. 6,255,115) and the treatment of protoplasts or spheroplasts with polyethylene glycol and $CaCl_2$ is described in Campbell, et al., (1989) *Curr. Genet.* 16:53-56, 1989 and Penttila, M. et al., (1988) *Gene,* 63:11-22.

Transformation and expression methods for bacteria are disclosed in Brigidi, DeRossi, Bertarini, Riccardi and Matteuzzi, (1990), *FEMS Microbiol. Lett.* 55: 135-138. A preferred general transformation and expression protocol for protease deleted *Bacillus* strains is provided in Ferrari et al., U.S. Pat. No. 5,264,366.

Transformation and expression in *Streptomyces* can be found in Hopwood et al., GENETIC MANIPULATION OF STREPTOMYCES: A LABORATORY MANUAL, (1985) John Innis Foundation, Norwich UK.

In other embodiments, transformation and expression in *Aspergillus* and *Trichoderma* is described in, for example U.S. Pat. Nos. 5,364,770; 6,022,725; and Nevalainen et al., 1992, The Molecular Biology of Trichoderma and its Application to the Expression of Both Homologous and Heterologous Genes, in MOLECULAR INDUSTRIAL MYCOLOGY, Eds. Leon and Berka, Marcel Dekker, Inc. pp. 129-148.

F. Host Cells

Host cells that may be used according to the invention include both bacterial and fungal cells. Preferred fungal host cells include filamentous fungal cells such as *Aspergillus* and *Trichoderma* cells. Preferred bacterial host cells include *Bacillus, Mycobacterium, Actinomyces* and *Streptomyces* cells. Particularly preferred host cells include *E. coli, B. subtilis, B. licheniformis, B. lentus, B. brevis, B. stearothermophilus, B. alkalophilus, B. amyloliquefaciens, B. coagulans, B. circulans, B. lautus, B. megaterium,* and *B. thuringiensis*. Particularly preferred host cells also include *Streptomyces* such as *S. griseus, S. lividans, S. coelicolor* and *S. avermitilis*.

In a particularly preferred embodiment, the host cell is a strain of *S. lividans* and most particularly strains TK23 and/or TK21.

G. Cell Culture

Host cells and transformed cells can be cultured in conventional nutrient media. The culture media for transformed host cells may be modified as appropriate for activating promoters and selecting transformants. The specific culture conditions, such as temperature, pH and the like, may be those that are used for the host cell selected for expression, and will be apparent to those skilled in the art. In addition, preferred culture conditions may be found in the scientific literature such as Sambrook, (1982) supra; Kieser, T, M J. Bibb, M J. Buttner, K F Chater, and D. A. Hopwood (2000) PRACTICAL STREPTOMYCES GENETICS. John Innes Foundation, Norwich UK; Harwood, et al., (1990) MOLECULAR BIOLOGICAL METHODS FOR BACILLUS, John Wiley and/or from the American Type Culture Collection (ATCC; "//www.atcc.org/"). Stable transformants of fungal host cells, such as *Trichoderma* cells can generally be distinguished from unstable transformants by their faster growth rate or the formation of circular colonies with a smooth rather than ragged outline on solid culture medium.

G. Recovery of Expressed Polypeptides

A polypeptide produced by the transformed host cell may be recovered from the culture medium by conventional procedures including separating the host cells from the medium by centrifugation or filtration, or if necessary, disrupting the cells and removing the supernatant from the cellular fraction and debris. Typically after clarification, the proteinaecous components of the supernatant or filtrate are precipitated by means of a salt, e.g., ammonium sulphate. The precipitated proteins are then solublized and may be purified by a variety of chromatographic procedures, e.g., ion exchange chromatography, gel filtration chromatography, affinity chromatography, and other art-recognized procedures. In some preferred embodiments, for the production of a cellulase it is preferred to cultivate the host cells under alkaline conditions using media containing a cellulase-based energy source.

In order to further illustrate the present invention and advantages thereof, the following specific examples are given with the understanding that they are being offered to illustrate the present invention and should not be construed in any way as limiting its scope.

EXAMPLES

Example 1

Isolation and Sequencing of the A4-L Promoter and A4 Promoter from *Aspergillus niger* Chromosomal DNA Isolation of *Aspergillus niger* chromosomal DNA—Genomic DNA from *Aspergillus niger* was isolated according to the procedure described in U.S. Pat. No. 6,399,329. The genomic DNA from a strain of *Aspergillus niger* was isolated. The fungal cells were grown in either CSL medium (Dunn-Coleman et al., (1991) *Bio/Technology* 9:976-981) for 2 to 4 days. The mycelia were harvested by filtering through Miracloth (Calbiochem). The genomic DNA was extracted from cells by repeated phenol/chloroform extraction according to the fungal genomic DNA purification protocol (Hynes et al., (1983) *Mol. Cell Biol.* 3: 1430-1439).

Restriction digestion of chromosomal DNA—The chromosomal DNA was digested with Sau3AIII for different periods of time and the digested DNA was run on agarose gel. Fragments from 400 bp to 1.2 kb were recovered from the gel and used for ligation.

Ligation and transformation—Digested chromosomal DNA was ligated to vector pIJ2587 digested by BamHI. The vector was provided by M. Bibb from The John Innes Center, Norwich, England and is disclosed in van Wezel G. P. et al., (2000) *J. Mol. Microbiol. Biotechnol.* (2000) 4:551-556. The vector was digested with BamHI and the ligation mixture was transformed into *Streptomyces lividans* TK23 protoplasts. The protoplasts were made from grown mycelium by addition of 400 µg/ml lysozyme in P buffer and incubation at 30° C. for up to 90 minutes. P Buffer includes 300 µl of 0.5% $KH_2PO_4$, 3 ml of 3.7% $CaCL_2.H_2O$, and 3 ml of 5.7% TES buffer, pH 7.2 into 24 ml $P_O$ buffer. $P_O$ buffer contains 103 g sucrose, 0.25 g $K_2SO_4$, 2 g $MgCl_2.H_2O$ and 2 ml of trace elements in 800 ml $H_2O$. The protoplasts were separated from mycelium by Mira Cloth filtration and concentrated further by centrifugation at 3000 rpm in 50 ml centrifuge tubes. 50 µl of protoplasts in the P buffer was mixed with DNA and 200 µl of T buffer (2.5 ml of 10.3% sucrose, 7.5 ml of $H_2O$, 20 µl of trace elements, 100 µl of 2.5% $K_2SO_4$, 550 µl of 1M Tris-maleic acid, pH 8.0, 220 µl of 5M $CaCL_2$ and 3.6 ml PEG1000) plated on R5 selection plates (R5 plate for 1 liter: 206 g sucrose, 0.5 g $K_2SO_4$, 20.24 g $MgCL_2$, 20 g glucose, 0.2 g Difco casamino acids, 10 g Difco yeast extracts and 11.46 g TES, 4 g L-Asp, 4 ml of trace elements and 44 g Difco agar in 800 ml $H_2O$. 20 ml 5% $K_2HPO_4$ and 8 ml 5M $CaCL_2.2H_2O$ and 14 ml 1N NaOH were added to a final 1 liter after autoclaving. After 20 hours a layer of thiostrepton (50 µg/ml final concentration) was plated on the top of the plates and incubated at 30° C. for 3 days (Kieser, T, M J. Bibb, M J. Buttner, K F Chater, and D. A. Hopwood (2000) PRACTICAL STREPTOMYCES GENETICS. John Innes Foundation, Norwich UK). Red colonies indicated promoter activity, while colonies with no promoter activity or colonies without inserted vectors did not appear red.

Isolation of Plasmids from *Streptomyces lividans* and Identification of the Promoters—

Red colonies grown on the plates were picked and the DNA was isolated by Qiagen spin column according to the procedure provided by the manufacturer, except that 400 ug/ml of lysozyme was added to the P1 buffer and incubated for 30 minutes at 37° C. before P2 buffer was added. The plasmid DNA was transformed into *E. coli* Top10 competent cells (Invitrogen). The plasmid then was isolated with Qiagen's spin column according to the instructions of the manufacturer. The DNA was submitted for DNA sequencing with the redD primer

```
(#147-RedDseq3:
AATATGTTGATTTCCATAAATTCCTC).      (SEQ ID NO: 6)
```

The redD primer, pairs with the beginning of the promoterless redD gene and reads towards the cloned promoter region. The A4-L sequence (SEQ ID NO: 1) was obtained from the sequencing reaction.

Homology search for the A4 promoter—The A4-L promoter sequence (SEQ ID NO: 1) was searched against the ERGO database. The cloned sequence of the promoter region (914 bp) contained two contiguous regions, contig 8165 and contig 9162, which were located in different regions of the *Aspergillus* chromosome (FIG. 2). Contig 8165 is 3988 bp and contig 9162 is 8140 bp. The first 419 bp of the A4-L promoter is located from 1214 bp to 793 bp in contig 9162 and the second part of the A4-L promoter (bp 420 to 829) is located at 3775 to 3365 bp of contig 9162. The two pieces of DNA each contain a Sau3A site at the ends. This indicates the two sequences were linked together due to the cloning procedure. There are minor differences in the sequence alignments.

A BLASTX search was performed for the two contigs. For the DNA in contig 8165, the homology search indicated 59% identity and 67% positives with a hypothetical protein AN4214.2 (Accession number EZZ59313) from *Aspergillus nidulans* Fungal Genetic Stock Center (FGSC) A4. The A4-L promoter region in contig 9162 was also searched using BLASTX. The DNA region has 77% identity and 91% positives with a hypothetical protein AN4908 from *Aspergillus nidulans* FGSC A4 (Accession number EAA60986). In both cases, the DNA piece of the promoter region goes in the opposite direction of the coding region of the hypothetical protein.

Example 2

Construction of Plasmids and Vectors Comprising the Promoters

This example describes the construction of plasmids comprising different regions of the A4-L promoter to determine activity and strength of the regions and to determine which piece was responsible for the A4-L promoter activity. The 5' region of the A4-L promoter is designated A4-5' and the 3' region of the A4-L promoter is designated A4.

A pSEGCT11AG8 vector containing a GI promoter as described in example 6 of U.S. Pat. No. 6,562,612 was used for these experiments and reference is made to FIGS. 3 and 4. The DNA fragments containing the A4 (SEQ ID NO: 2), the A4-5' (SEQ ID NO: 3) and A4-L (SEQ ID NO: 1) promoters were cloned into pSEGCT11AG8 at the XbaI and Eco47III site, replacing the GI promoter. The resulting plasmids included the 11AG8 gene immediate downstream of the promoter.

To make A4-5' promoter constructs the following two primers were used:

```
342(A4a-5'XbaI):
                                           (SEQ ID NO: 7)
GGTCTAGAAAACACCACCCAGCTCGCTG
and 343 (A4a-3' Eco47III):
                                           (SEQ ID NO: 8)
GGAGCGCTCCCAAAGCCCATGGTTACCTCCGGGATCGGGAGTTTGCTCCG

CTAG.
```

To make the A4 promoter construct the following primers were used:

```
344 (A4b-5'XbaI):
                                           (SEQ ID NO: 9)
GGTCTAGAGATCGAACTTCATGTTCGAGTTC
and 345 (A4b-3'Eco47III):
                                           (SEQ ID NO: 10)
GGAGCGCTCCCAAAGCCCATGGTTACCTCCGGGGGTCTGTCTCTGCACGA

TGCC.
```

To make the A4-L promoter construct primers 342 (SEQ ID NO: 7) and 345 (SEQ ID NO: 10) were used. This construct contains 724 nucleotides instead of 914 bp. The 3' region from 824 to 914 bp (FIG. 2) of the full length promoter was not included.

The A4 containing vector was designated pA4-11AG8-4, the A4-L containing vector was designated pA4-11AG8-5, and the A4-5' containing vector was designated pA4-11AG8-2.

*Streptomyces lividans* cells were transformed with the A4, A4-5' and A4-L vectors as described above. Selected colonies having a functional promoter and therefore appearing red on selection plates were grown in TS in shake flasks for three days in the presence of 50 ug/ml thiostrepton at 30° C. Cells were then transferred to a medium free of antibiotics and growth was continued for another three days. Samples were taken for 11AG8 enzyme activity assay.

TS=16 g Difco tryptone, 4 g Difco soytone, 20 g caseine (hydolysate) sigm and 5 g $K_2HPO_4$ brought to 1 liter. After autoclaving 50% filtered sterilized glucose was added to a final concentration of 1.5%.

The 11AG8 cellulase was assayed on a Monarch assay machine (Instrumentation Laboratory Company, Mass.). One ml of sample was taken from each shake flask and centrifuged at 14,000 rpm. Part of the supernatant was used for the enzyme assay. Samples were loaded into different wells, and after one minute incubation at 30° C., the substrates were mixed with the samples and reaction was monitored every 10 seconds for 15 different time points. The $OD_{405}$ was measured and converted to units per ml after comparison with known concentration of the enzyme standard. The specific activity (U/mg/ml) was calculated by dividing the enzyme activity by the dry cell weight. Relative activity of samples was calculated using 11AG8 as 100 percent of activity.

The detailed assay is as follows: Dilution buffer: 100 mM Sodium Phosphate, pH 8.0 and 0.2 um filter sterilized was used to dilute the samples and substrate. The dilution buffer was prepared by mixing 12 g $NaH_2PO_4$ in 800 ml de-ionized water and pH adjust up to pH 8.0 with 6N NaOH was brought to 1.0 L final volume and then 0.2 um filter sterilized. Substrate: o-Nitrophenyl D-Cellobioside (o-NPC) (Sigma N-4764), 500 mg bottle, store in −20° C. freezer. 4.167 mg/ml buffer/substrate solution was made up for Monarch boats: To a 500 mg bottle of o-NPC substrate, 10 ml buffer was added. The solution was dissolved and transferred to 200 ml bottles. This was repeated 2× (10 mls each) to rinse the bottle. 90 ml of buffer was added to bring the substrate to final concentration of 500 mg in 120 ml buffer. 12 ml aliquots were placed in 15 ml conical tubes and frozen at −20 C. The Monarch boats were refilled thawing out and topping up with 15 ml tubes as needed. Standards: Four standards with different concentration of 11AG8 enzymes from a previously quantified fermentation sample were used 18.90 U/ml, 55.88 U/ml, 99.09 U/ml, and 157.38 U/ml.

Figure 5:
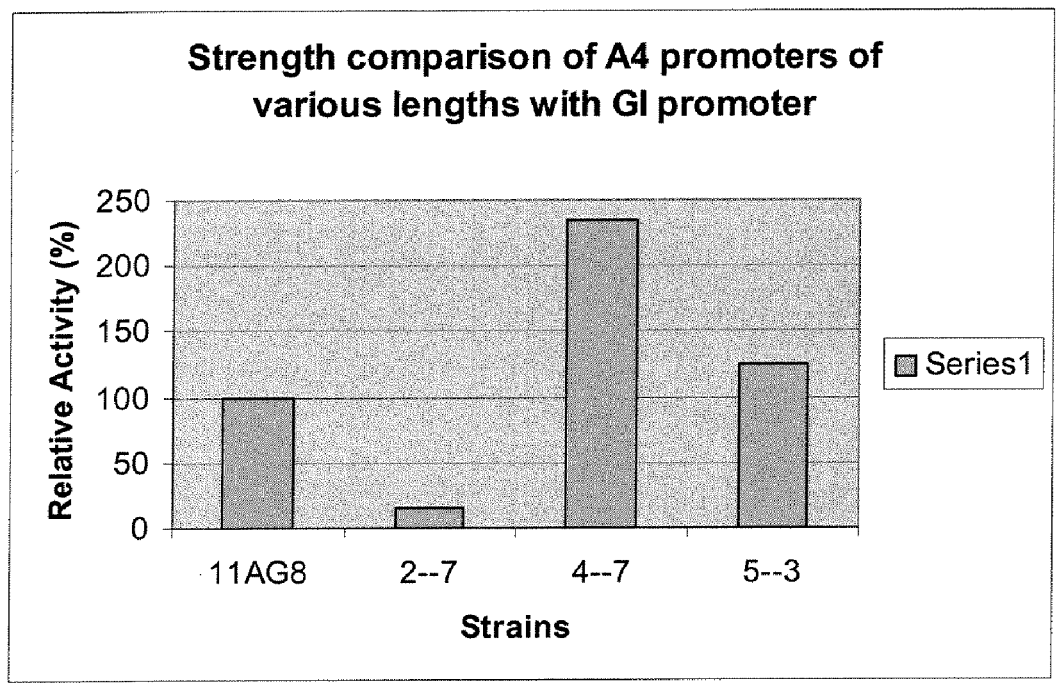
FIG. 5 shows the comparison of promoter strength as % relative activity of 11AG8 in *S. lividans* TK23 host cells. 11AG8 represents host cells transformed with a vector having the GI promoter (pSEQCT11AG8), 2-7 represents host cells transformed with a vector having the A4-5' promoter (pA411AG8-2); 4-7 represents host cells transformed with a vector having the A4 promoter (pA411AG8-4) and 5-3 represents host cells transformed with a vector having the A4-L promoter (pA411AG8-5).

The results of the shake flask experiments as described above show that the % relative cellulase 11AG8 activity is 2-fold greater with the A4 promoter compared to the GI promoter (FIG. 5).

Figure 6A:
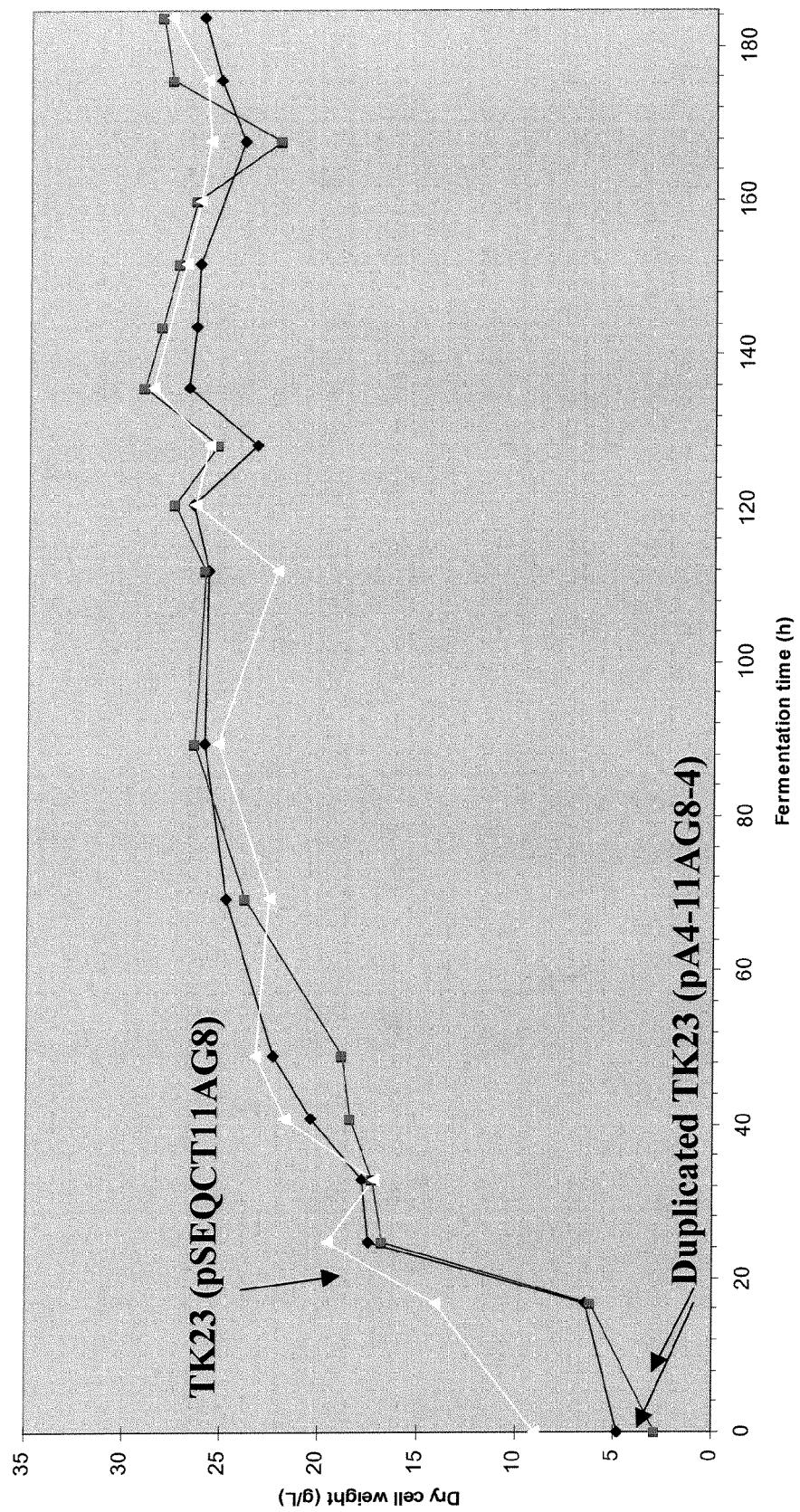
FIG. 6A illustrates the comparison of dry cell weight in *S. lividans* TK23 cells transformed with either the vector comprising the GI promoter or the vector comprising the A4 promoter.
Figure 6B:
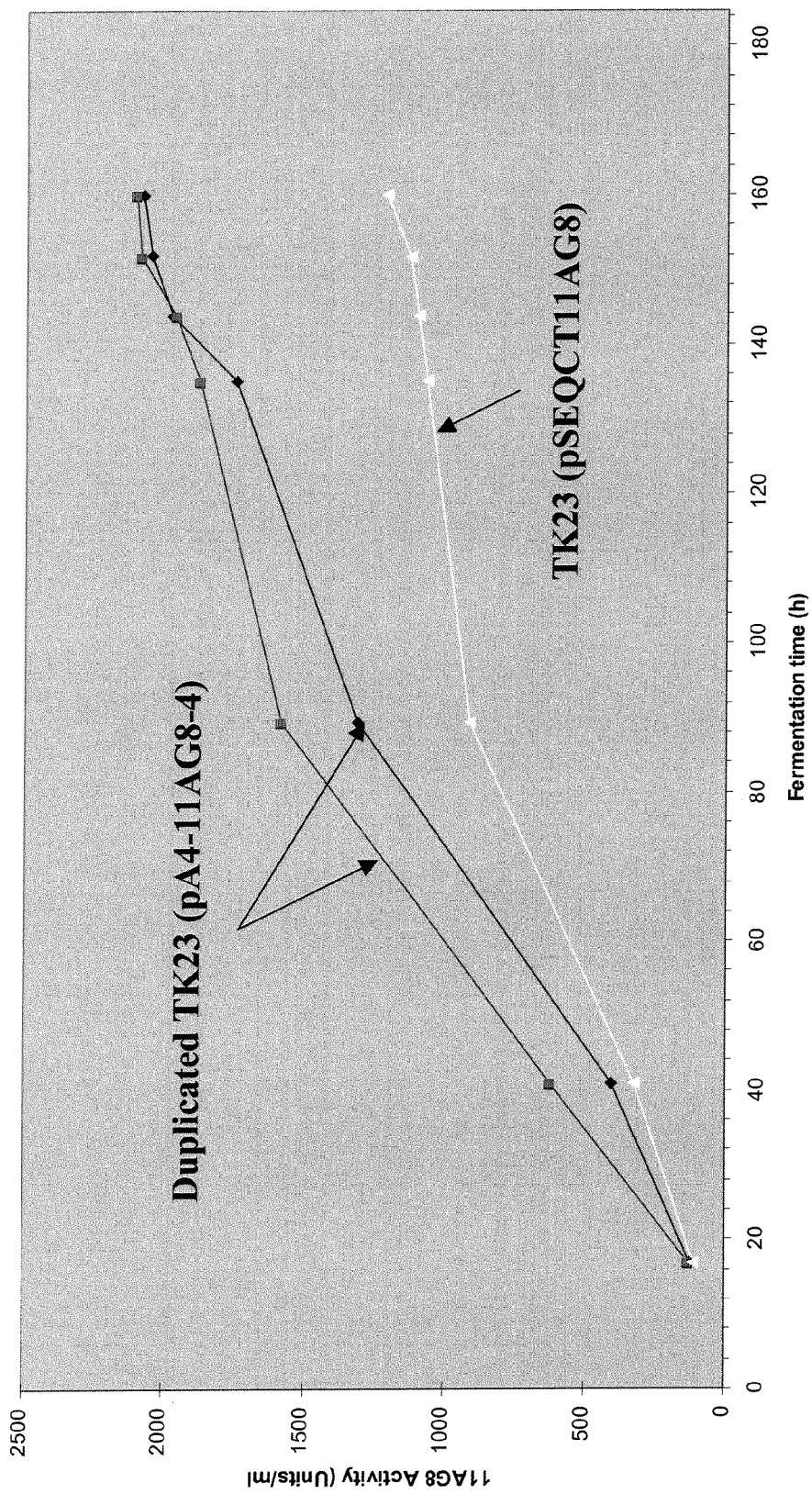
FIG. 6B illustrates the comparison of 11AG8 activity from *S. lividans* TK23 cells transformed with either the vector comprising the GI promoter or the vector comprising the A4 promoter.

Additionally fermentation cultures were run with the transformed cultures. At various time points, samples of the fermentation broths were removed for analysis. FIG. 6A shows the dry cell weight for cells transformed with the vector comprising the GI promoter and for cells transformed with the vector comprising the A4 promoter (pA4-11AG8-4). FIG. 6B illustrates that the production of 11AG8 in cells transformed with the vector comprising the A4 promoter (pA4-

11AG8-4) was double that of the production of 11AG8 for the vector comprising the GI promoter (pSEQCT11AG8).

Example 3

Protease Production in *Streptomyces lividans* with a Vector Comprising the A4 Promoter This Example describes experiments conducted to determine production of a protease by *S. lividans* transformed with a vector comprising the A4 promoter or the GI promoter operably linked to a gene encoding a *Cellulomonas* 69B4 protease designated asp. The plasmid comprising the GI promoter and developed during these experiments was designated as "pSEG69B4". The plasmid comprising the A4 promoter and developed during these experiments was designated "pSEA469B4T" (or "pSEA469B4CT") (FIGS. 7A-B).

The following sequence (SEQ ID NO: 11) is the amino acid sequence of the mature protease derived from *Cellulomonas* strain 69B4 (DSM 16035).

```
                                              (SEQ ID NO: 11)
FDVIGGNAYT IGGRSRCSIG FAVNGGFITA GHCGRTGATT

ANPTGTFAGS SFPGNDYAFV RTGAGVNLLA QVNNYSGGRV

QVAGHTAAPV GSAVCRSGST TGWHCGTITA LNSSVTYPEG

TVRGLIRTTV CAEPGDSGGS LLAGNQAQGV TSGGSGNCRT

GGTTFFQPVN PILQAYGLRM ITTDSGSSP
```

The following sequence (SEQ ID NO: 12) is the amino acid sequence of the signal peptide of the protease derived from *Cellulomonas* strain 69B4 (DSM 16035).

```
MTPRTVTRAL AVATAAATLL AGGMAAQA    (SEQ ID NO: 12)
```

The construction of both the pSEG69B4 and pSEA469B4T plasmids made use of pSEGCT (See, WO 02/50245 and U.S. Pat. No. 6,562,612). With respect to pSEG69B4, a glucose isomerase promoter was operably linked to the structural gene encoding a 69B4 protease (SEQ ID NO. 11) to drive the expression of the protease. A fusion between the GI promoter and the 69B4 signal sequence, N-terminal prosequence and mature sequence was constructed by fusion-PCR techniques as a XbaI-BamHI fragment. The fragment was ligated into plasmid pSEGCT digested with XbaI and BamHI, resulting in plasmid pSEG69B4. With respect to pSEA469B4T, the A4 promoter encompassed by the invention (SEQ ID NO: 2) was operably linked to the structural gene encoding the 69B4 protease (SEQ ID NO: 11) to drive the expression of the protease. A fusion between the A4 promoter and the CelA signal sequence from *Streptomyces lividans*, N-terminal prosequence and mature sequence was constructed by fusion PCR techniques, as a XbaI-BamHI fragment. The fragment was ligated into plasmid pSEA4CT digested with XbaI and BamHI, resulting in plasmid pSEA469B4T.

In these experiments, the host *Streptomyces lividans* TK23 was transformed with either of the vectors described above. The transformation techniques were the protoplast method described in Hopwood, et al., GENETIC MANIPULATION OF STREPTOMYCES, A LABORATORY MANUAL. The John Innes Foundation, Norwich, United Kingdom (1985).

The transformed culture was expanded to provide two fermentation cultures. At various time points, samples of the fermentation broths were removed for analysis. For the purposes of this experiment, a skim milk procedure was used to confirm successful cloning. 30 µl of the shake flask supernatant was spotted in punched out holes in skim milk agar plates and incubated at 37° C. The incubated plates were visually reviewed after overnight incubation for the presence of halos. For purposes of this experiment, the samples were also assayed for protease activity and for molecular weight (SDS-PAGE). At the end of the fermentation run, full length protease was observed by SDS-PAGE.

A sample of the fermentation broth was assayed as follows: 10 µl of the diluted supernatant was taken and added to 190 µl AAPF substrate solution (conc. 1 mg/ml, in 0.1 M Tris/0.005% Tween, pH 8.6).

The rate of increase in absorbance at 410 nm due to release of p-nitroaniline was monitored (25°). The assay results of the fermentation broth of 3 clones (X, Y, W) obtained using the pSEG69B4T plasmid are shown in Table 2, below.

TABLE 2

| Results for Three Clones using pSEG69B4 | |
|---|---|
| CLONE | Total mOD/min |
| V | 23296 |
| W | 19224 |
| Y | 13171 |

The assay results of the fermentation broth of 2 clones (C1 and C2) obtained using the pSEA469B4T plasmid are shown in Table 3, below.

TABLE 3

| Results for Two Clones using pSEA469B4T | |
|---|---|
| CLONE | Total mOD/min |
| C1 | 29804 |
| C2 | 35685 |

Thus, these results show that the polynucleotide encoding a polypeptide having proteolytic activity was expressed in *Streptomyces lividans* using both expression vectors. However, activity of the proteolytic polypeptide using pSEA469B4T, which comprises the A4 prompter of the invention was significantly greater than activity using pSEG69B4, which comprises the GI promoter indicating that the A4 promoter was stronger than the GI promoter.

The invention claimed is:

1. An isolated nucleic acid comprising the nucleotide sequence of SEQ ID NO:2 or a variant having 90% sequence identity.

2. A recombinant nucleic acid comprising:
the isolated nucleic acid of claim 1; and
a polynucleotide encoding a protein;
wherein said isolated nucleic acid and said polynucleotide are operably linked such that said isolated nucleic acid causes transcription of said polynucleotide.

3. The recombinant nucleic acid of claim 2, wherein said protein is a heterologous protein.

4. The recombinant nucleic acid of claim 2, wherein said protein is an enzyme.

5. The recombinant nucleic acid of claim 2, wherein said protein is a reporter.

6. The recombinant nucleic acid of claim 2, wherein said protein is a fusion protein.

7. The recombinant nucleic acid of claim 3, wherein said protein comprises a signal sequence.

8. A vector comprising the recombinant nucleic acid of claim 2.

9. A host cell comprising the recombinant nucleic acid of claim 2.

10. The host cell of claim 9, wherein said recombinant nucleic acid is present in a genome of said cell.

11. The host cell of claim 9, wherein said recombinant nucleic acid is present in a vector that replicates in said cell.

12. The host cell of claim 9, wherein said host cell is a filamentous fungal host cell.

13. A method of producing a protein in a host cell, comprising:
transforming said host cell with the recombinant nucleic acid of claim 3;
growing said host cell in a culture medium under conditions in which the protein is produced.

14. The method of claim 13, further comprising:
recovering said protein from said culture medium.

* * * * *

SEQUENCE LISTING

<160> NUMBER OF SEQ ID NOS: 12

<210> SEQ ID NO 1
<211> LENGTH: 914

```
<212> TYPE: DNA
<213> ORGANISM: Aspergillus niger

<400> SEQUENCE: 1
aaacaccacc cagctcgctg aaaaaacaaa tccacaatgc aggaaatagg tatcttaaat      60
gacggacata tgccactcaa aacgaatgcg tcctccccct acatcacgat gcagcatccg     120
cagcccttct ccttcggcgg cggttcctgc gcggtcacca ctggcgggct ccatttcggc     180
tgcagtgccg cctgtggtgg ttcctgtacc cgcggcatcg tgctgtagcc ggtgcctgag     240
ttcggccgtc ccgactcctt ggacggtgtc tccaaattcg gggtcttctg tggctcttgc     300
acttcttcct tctcctcctt ttcgttctgt tcgatcggct ccggctccac ttccttcggt     360
gccggcttct ctgtgggctt cggcccgtct ggcccaatgg ctagcggagc aaactcccga     420
tcgaacttca tgttcgagtt cttgttcacg tagaagccgg agatgtgaga ggtgatctgg     480
aactgctcac cctcgttggt ggtgacctgg aggtaaagca agtgacccct ctggcggagg     540
tggtaaggaa cggggttcca cggggagaga gagatggcct tgacggtctt gggaaggggga     600
gcttcggcgc gggggaggat ggtcttgaga gaggggagc tagtaatgtc gtacttggac     660
agggagtgct ccttctccga cgcatcagcc acctcagcgg agatggcatc gtgcagagac     720
agaccagcgc tgataccatg gaggttgtca acccggtcac ccgcagcgcc aaccagctct     780
ctcatgcgaa caacgtgcat acgagcttcc ttctcgttgt agggatcctg cagggctaac     840
ctgatcctct agggacttaa cagcaaagat cacctggcgc cgattgaacc aaggcgtaca     900
gaaccactcc acag                                                      914

<210> SEQ ID NO 2
<211> LENGTH: 365
<212> TYPE: DNA
<213> ORGANISM: Aspergillus niger

<400> SEQUENCE: 2
tgccggcttc tctgtgggct tcggcccgtc tggcccaatg gctagcggag caaactcccg      60
atcgaacttc atgttcgagt tcttgttcac gtagaagccg gagatgtgag aggtgatctg     120
gaactgctca ccctcgttgg tggtgacctg gaggtaaagc aagtgaccct ctggcggag      180
gtggtaagga acggggttcc acggggagag agagatggcc ttgacggtct tgggaagggg     240
agcttcggcg cggggaggga tggtcttgag agaggggag ctagtaatgt cgtacttgga     300
cagggagtgc tccttctccg acgcatcagc cacctcagcg gagatggcat cgtgcagaga     360
cagac                                                                365

<210> SEQ ID NO 3
<211> LENGTH: 359
<212> TYPE: DNA
<213> ORGANISM: Aspergillus niger

<400> SEQUENCE: 3
aaacaccacc cagctcgctg aaaaaacaaa tccacaatgc aggaaatagg tatcttaaat      60
gacggacata tgccactcaa aacgaatgcg tcctccccct acatcacgat gcagcatccg     120
cagcccttct ccttcggcgg cggttcctgc gcggtcacca ctggcgggct ccatttcggc     180
tgcagtgccg cctgtggtgg ttcctgtacc cgcggcatcg tgctgtagcc ggtgcctgag     240
ttcggccgtc ccgactcctt ggacggtgtc tccaaattcg gggtcttctg tggctcttgc     300
acttcttcct tctcctcctt ttcgttctgt tcgatcggct ccggctccac ttccttcgg      359
```

<210> SEQ ID NO 4
<211> LENGTH: 1715
<212> TYPE: DNA
<213> ORGANISM: Artificial Sequence
<220> FEATURE:
<223> OTHER INFORMATION: synthetic expression cassette

<400> SEQUENCE: 4

```
ctagagtcga ccacgcaggc cgccaggtag tcgacgttga tctcgcagcc gagcccggcc      60
ggaccggcgg cgctgagcgc gaggccgacg gcgggacggc cggcaccggt acgcggtggc     120
gggtcgagtt cggtgagcag cccaccggcg atcaggtcgt cgacgagcgc ggagacggtg     180
gcccgggtga gcccggtgac ggcggcaact cccgcgcggg agagccgatc tgtgctgttt     240
gccacggtat gcagcaccag cgcgagatta tgggctcgca cgctcgactg tcggacgggg     300
gcactggaac gagaagtcag gcgagccgtc acgcccttga caatgccaca tcctgagcaa     360
ataattcaac cactaaacaa atcaaccgcg tttcccggag gtaaccatgg ctttgggag      420 cgctcccatc gcgttgtgtc cgcttcgcac gaggaggaac gctttgaaac gccttttggc     480
cctgctcgcg accggcgtgt cgatcgtcgg cctgactgcg ctagccggcc ccccggcaca     540
ggccaaccag cagatctgcg accgctacgc caccaccacg atccaggacc ggtacgtggt     600
gcagaacaac cgctggggca ccagcgccac ccagtgcatc aatgtgaccg gcaacggttt     660
cgagatcacc caggccgacg gttcggtgcc gaccaacggc gccccgaagt cctatccctc     720
ggtctacgac ggctgccact acggcaactg cgcgccccgc acgacgctgc ccatgcggat     780
cagctcgatc ggcagcgcgc ccagcagtgt ctcctaccgc tacaccggca acggcgtcta     840
caacgccgcg tacgacatct ggctggaccc gacaccccgc accaacgggg tgaaccggac     900
cgagatcatg atctggttca accgggtcgg cccggtccag cccatcggtt cgccggtcgg     960
cacggcccac gtcggcggcc gcagctggga ggtgtggacc ggcagcaacg gttcgaacga    1020
cgtgatctcc ttcctggcgc cctcgcgat cagcagctgg agcttcgacg tcaaggactt     1080
cgtcgaccag gccgtcagcc acggcctggc caccccggac tggtacctca ccagcatcca    1140
ggcgggcttc gagccgtggg agggcggcac cggtctggcc gtgaactcgt tctcctccgc    1200
ggtgaacgcc gggggcggga acggcggcac tccggggaca ccggcggcct gccaggtctc    1260
ctacagcacc cacacctggc ccggcggctt caccgtcgac accaccatca ccaataccgg    1320
ctccacaccc gtcgacggct gggaactgga cttcaccctc cccgccggtc acacggtcac    1380
cagcgcgtgg aacgcgctga tcagccccgc ctcgggcgcg gtcacggcac gcagcaccgg    1440
ttccaacggc cggatcgcgg ccaacggcgg gacccagtcc ttcggtttcc agggcaccctc   1500 cagcggaacg gggttcaacg caccggccgg gggccggctc aacggcacct cctgcacagt    1560
gagatgacaa tggggatccg cgagcggatc ggctgaccgg agcggggagg aggacgggcg    1620
gccggcggaa aagtccgccg gtccgctgaa tcgctccccg ggcacggacg tggcagtatc    1680
agcgccatgt ccggcatatc ccagccctcc gcatg                                1715
```

<210> SEQ ID NO 5
<211> LENGTH: 386
<212> TYPE: PRT
<213> ORGANISM: Artificial Sequence
<220> FEATURE:
<223> OTHER INFORMATION: CelA-11AG8 protein sequence

<400> SEQUENCE: 5

```
Met Gly Phe Gly Ser Ala Pro Ile Ala Leu Cys Pro Leu Arg Thr Arg
 1               5                  10                  15
```

```
Arg Asn Ala Leu Lys Arg Leu Leu Ala Leu Ala Thr Gly Val Ser
         20                  25                  30

Ile Val Gly Leu Thr Ala Leu Ala Gly Pro Pro Ala Gln Ala Asn Gln
             35                  40                  45

Gln Ile Cys Asp Arg Tyr Gly Thr Thr Thr Ile Gln Asp Arg Tyr Val
 50                      55                  60

Val Gln Asn Asn Arg Trp Gly Thr Ser Ala Thr Gln Cys Ile Asn Val
 65                  70                  75                  80

Thr Gly Asn Gly Phe Glu Ile Thr Gln Ala Asp Gly Ser Val Pro Thr
                 85                  90                  95

Asn Gly Ala Pro Lys Ser Tyr Pro Ser Val Tyr Asp Gly Cys His Tyr
                100                 105                 110

Gly Asn Cys Ala Pro Arg Thr Thr Leu Pro Met Arg Ile Ser Ser Ile
             115                 120                 125

Gly Ser Ala Pro Ser Ser Val Ser Tyr Arg Tyr Thr Gly Asn Gly Val
         130                 135                 140

Tyr Asn Ala Ala Tyr Asp Ile Trp Leu Asp Pro Thr Pro Arg Thr Asn
145                 150                 155                 160

Gly Val Asn Arg Thr Glu Ile Met Ile Trp Phe Asn Arg Val Gly Pro
                165                 170                 175

Val Gln Pro Ile Gly Ser Pro Val Gly Thr Ala His Val Gly Gly Arg
            180                 185                 190

Ser Trp Glu Val Trp Thr Gly Ser Asn Gly Ser Asn Asp Val Ile Ser
        195                 200                 205

Phe Leu Ala Pro Ser Ala Ile Ser Ser Trp Ser Phe Asp Val Lys Asp
210                 215                 220

Phe Val Asp Gln Ala Val Ser His Gly Leu Ala Thr Pro Asp Trp Tyr
225                 230                 235                 240

Leu Thr Ser Ile Gln Ala Gly Phe Glu Pro Trp Gly Gly Thr Gly
                245                 250                 255

Leu Ala Val Asn Ser Phe Ser Ser Ala Val Asn Ala Gly Gly Asn
                260                 265                 270

Gly Gly Thr Pro Gly Thr Pro Ala Ala Cys Gln Val Ser Tyr Ser Thr
        275                 280                 285

His Thr Trp Pro Gly Gly Phe Thr Val Asp Thr Ile Thr Asn Thr
        290                 295                 300

Gly Ser Thr Pro Val Asp Gly Trp Glu Leu Asp Phe Thr Leu Pro Ala
305                 310                 315                 320

Gly His Thr Val Thr Ser Ala Trp Asn Ala Leu Ile Ser Pro Ala Ser
                325                 330                 335

Gly Ala Val Thr Ala Arg Ser Thr Gly Ser Asn Gly Arg Ile Ala Ala
                340                 345                 350

Asn Gly Gly Thr Gln Ser Phe Gly Phe Gln Gly Thr Ser Ser Gly Thr
                355                 360                 365

Gly Phe Asn Ala Pro Ala Gly Gly Arg Leu Asn Gly Thr Ser Cys Thr
            370                 375                 380

Val Arg
385

<210> SEQ ID NO 6
<211> LENGTH: 26
<212> TYPE: DNA
<213> ORGANISM: Artificial Sequence
<220> FEATURE:
<223> OTHER INFORMATION: primer
```

-continued

<210> SEQ ID NO 6
<400> SEQUENCE: 6
aatatgttga tttccataaa ttcctc                                        26

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7
ggtctagaaa acaccaccca gctcgctg                                      28

<210> SEQ ID NO 8
<211> LENGTH: 54
<212> TYPE: DNA
<213> ORGANISM: Artificial Sequence
<220> FEATURE:
<223> OTHER INFORMATION: primer

<400> SEQUENCE: 8
ggagcgctcc caaagcccat ggttacctcc gggatcggga gtttgctccg ctag          54

<210> SEQ ID NO 9
<211> LENGTH: 31
<212> TYPE: DNA
<213> ORGANISM: Artificial Sequence
<220> FEATURE:
<223> OTHER INFORMATION: primer

<400> SEQUENCE: 9
ggtctagaga tcgaacttca tgttcgagtt c                                  31

<210> SEQ ID NO 10
<211> LENGTH: 54
<212> TYPE: DNA
<213> ORGANISM: Artificial Sequence
<220> FEATURE:
<223> OTHER INFORMATION: primer

<400> SEQUENCE: 10
ggagcgctcc caaagcccat ggttacctcc gggggtctgt ctctgcacga tgcc          54

<210> SEQ ID NO 11
<211> LENGTH: 189
<212> TYPE: PRT
<213> ORGANISM: Artificial Sequence
<220> FEATURE:
<223> OTHER INFORMATION: mature protease derived from Cellulomonas
      strain

<400> SEQUENCE: 11

Phe Asp Val Ile Gly Gly Asn Ala Tyr Thr Ile Gly Gly Arg Ser Arg
 1               5                  10                  15

Cys Ser Ile Gly Phe Ala Val Asn Gly Gly Phe Ile Thr Ala Gly His
             20                  25                  30

Cys Gly Arg Thr Gly Ala Thr Thr Ala Asn Pro Thr Gly Thr Phe Ala
         35                  40                  45

Gly Ser Ser Phe Pro Gly Asn Asp Tyr Ala Phe Val Arg Thr Gly Ala
     50                  55                  60

Gly Val Asn Leu Leu Ala Gln Val Asn Asn Tyr Ser Gly Gly Arg Val
 65                  70                  75                  80

Gln Val Ala Gly His Thr Ala Ala Pro Val Gly Ser Ala Val Cys Arg
                 85                  90                  95

```
Ser Gly Ser Thr Thr Gly Trp His Cys Gly Thr Ile Thr Ala Leu Asn
            100                 105                 110

Ser Ser Val Thr Tyr Pro Glu Gly Thr Val Arg Gly Leu Ile Arg Thr
        115                 120                 125

Thr Val Cys Ala Glu Pro Gly Asp Ser Gly Gly Ser Leu Leu Ala Gly
    130                 135                 140

Asn Gln Ala Gln Gly Val Thr Ser Gly Gly Ser Gly Asn Cys Arg Thr
145                 150                 155                 160

Gly Gly Thr Thr Phe Phe Gln Pro Val Asn Pro Ile Leu Gln Ala Tyr
                165                 170                 175

Gly Leu Arg Met Ile Thr Thr Asp Ser Gly Ser Ser Pro
            180                 185

<210> SEQ ID NO 12
<211> LENGTH: 28
<212> TYPE: PRT
<213> ORGANISM: Artificial Sequence
<220> FEATURE:
<223> OTHER INFORMATION: signal peptide of the protease derived from
      Cellulomonas strain

<400> SEQUENCE: 12

Met Thr Pro Arg Thr Val Thr Arg Ala Leu Ala Val Ala Thr Ala Ala
1               5                   10                  15

Ala Thr Leu Leu Ala Gly Gly Met Ala Ala Gln Ala
            20                  25
```